(12) United States Patent
Bentley

(10) Patent No.: US 6,705,727 B1
(45) Date of Patent: Mar. 16, 2004

(54) MECHANISM FOR ROTATIONALLY MOVING A MIRROR

(75) Inventor: Joseph R. Bentley, West Jordan, UT (US)

(73) Assignee: Bausch & Lomb Incorporated, Rochester, NY (US)

( * ) Notice: Subject to any disclaimer, the term of this patent is extended or adjusted under 35 U.S.C. 154(b) by 0 days.

(21) Appl. No.: 10/335,025

(22) Filed: Dec. 30, 2002

(51) Int. Cl.[7] ................................................ A61B 3/10
(52) U.S. Cl. ...................................... 351/220; 359/198
(58) Field of Search ................................. 356/300, 334; 359/196, 198, 200, 212; 351/205, 214, 220, 245; 294/64.1

(56) References Cited

U.S. PATENT DOCUMENTS

| | | | |
|---|---|---|---|
| 3,680,461 A | 8/1972 | Amesbury et al. | 95/37 |
| 3,840,300 A | 10/1974 | Vane | 355/53 |
| 3,843,259 A | 10/1974 | Tohyama et al. | 356/97 |
| 4,511,205 A | 4/1985 | Crane | 350/6.1 |
| 4,588,887 A | 5/1986 | Bailey et al. | 250/236 |
| 4,750,486 A | 6/1988 | Butler et al. | 128/303.1 |
| 5,192,981 A | 3/1993 | Slutter et al. | 356/334 |
| 5,221,933 A | 6/1993 | Chandler et al. | 346/109 |
| 5,235,180 A | 8/1993 | Montagu | 250/231.13 |
| 5,587,094 A | 12/1996 | Yoshida et al. | 219/121.68 |
| 6,203,082 B1 * | 3/2001 | Bendat et al. | 294/64.1 |
| 6,490,072 B2 * | 12/2002 | Chee | 359/198 |
| 2002/0143506 A1 | 10/2002 | D'Aligny et al. | 703/5 |

* cited by examiner

Primary Examiner—George Manuel
(74) Attorney, Agent, or Firm—Michael L. Smith

(57) ABSTRACT

A device 10 for rotationally moving a mirror includes a mirror mount 20 connected to a pivot lever 22. A motor 12 having a lead-screw 14 moves the lead-screw in a linear manner along an axis 26. An elongated angled member 18 is connected to the lead-screw 14 and abuts the pivot lever 22. The elongated angled member 18 is set at a non-parallel angle with respect to the lead-screw 14 so that as the lead-screw 14 is moved along its axis 26 the elongated angled member 18 causes the pivot lever 22 to pivot, and in turn, causes the mirror 20 to rotate.

12 Claims, 2 Drawing Sheets

MECHANISM FOR ROTATIONALLY MOVING A MIRROR

BACKGROUND OF THE INVENTION

1. Field of the Invention

The present invention relates to mechanisms for rotationally moving an object. More specially, the present invention relates to a mechanism for rotationally moving a mirror for effecting the scanning of a slit of light across a patient's cornea.

2. Description of Related Art

In certain applications it is important to control the angular position of a rotating element with high accuracy and precision. For example, in ophthalmic diagnostic equipment such as a corneal topographer, it is necessary to rotate or scan a light slit across the cornea of the eye. For example, the ORBSCAN™ Corneal Topographer available from Bausch & Lomb Incorporated scans a slit of light across the cornea of a patient's eye.

Typically in the prior art, such devices as Galvanometers have provided precision angular position detection in order to provide a discreet and accurate rotation of such devices as mirrors. Galvanometers typically achieve their accuracy using variable-inductance transducers or variable-capacitance transducers. These Galvanometers typically depend on change in inductance or capacitance in the angular position of a rotor of an electrical motor to determine the position of the rotor. While these Galvanometer rotating systems are highly accurate, they are also costly and their size can be of concern, especially in ophthalmic applications where smaller size allows easy measurement of an eye.

Therefore, it would advantageous to have a mechanism to rotationally move a mirror in order to scan light, especially a slit of light across the cornea of an eye using a compact and cost effective design.

DETAILED DESCRIPTION OF THE PREFERRED EMBODIMENT

Figure 1:
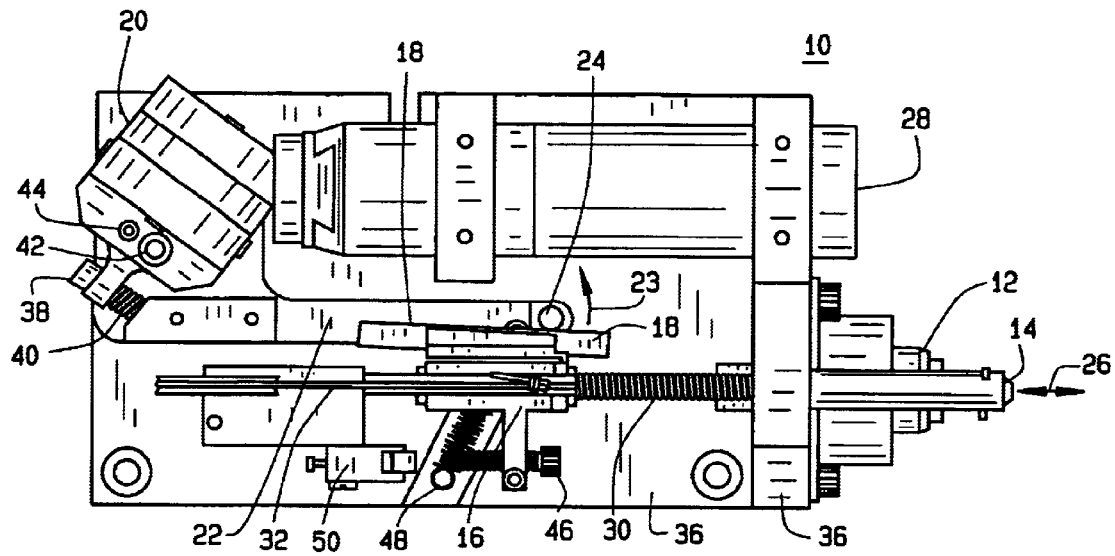
FIG. 1 is a top view of a mechanism in accordance with the present invention.

Mechanism 10 includes a stepper-motor 12, a lead-screw 14, and an angled pin carriage 16 for carrying elongated angled member 18 also referred to herein as angled pin 18. A mirror mount 20 including a mirror (not shown) is connected to a pivot lever 22 which abuts angled pin 18 via dowel 24.

Motor 12 has a lead-screw 14 and causes lead-screw 14 to move in a linear manner along axis 26. Elongated angle member 18 is connected to the lead-screw 14 via carriage 16 and abuts the pivot lever 22. As can be seen in FIG. 1, elongated angled member 18 is set at a non-parallel angle preferably 2.5° with respect to lead-screw 14, such that as lead-screw 14 is moved along its axis 26, elongated angled member 18 causes the pivot lever 22 to pivot in the direction of arrow 23 and, in turn, causes the mirror 20 to rotate. The pivot point of lever 22 is not shown and preferably is below mirror 20.

Preferably, mechanism 10 also includes a light source 28 associated with the mirror mount 20, such that upon rotation the mirror reflects the light source over a known angle range. Also preferably, light source 28 is a slit light source known in the prior art such as white light, xenon, laser light or other suitable source. Preferably, motor 12 is a stepper-motor able to rotate the mirror in discreet increments model L-92141P1 available from Thomson Airpax.

In addition, mechanism 10 preferably includes an anti-backlash, biased spring 30 and cord 32 that rotates about wheel 34 and is connected to a housing 36 and lead-screw 14 to prevent backlash. Preferably mirror mount 20 includes a mirror angle adjusting screw 38 and spring 40 as well as mirror tilt-adjusting screws 42 and 44. The mechanism 10 also preferably includes a motor zero screw 46 and a lever biased spring 48.

Figure 2:
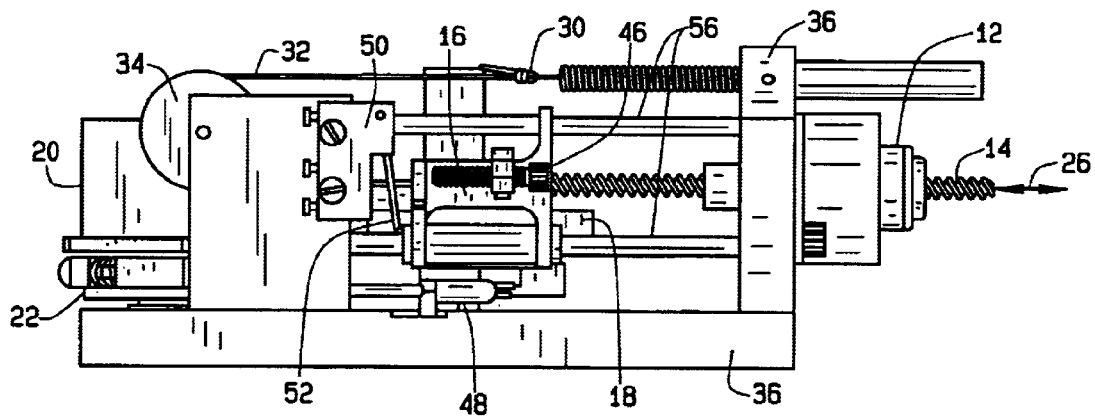
FIG. 2 is a side view of FIG. 1.

In operation, mechanism 10, through stepper-motor 12, receives a series of electrical pulses in a particular sequence causing lead-screw 14 to extend. This in turn, moves angled pin carriage 16 and angled pin 18 in the direction of micro-switch 50 until motor zero screw 46 engages the micro-switch 52. Mechanism 10 is then at its mechanical and electrical zero. Each electrical pulse received in a sequence opposite that of the preceding sequence received by stepper-motor 12 will move angled pin carriage 16 in a finite known distance away from micro-switch 52. Carriage 16 preferably rides along guide rails 56 as shown in FIG. 2.

The angled pin 18 will deflect the lever 22 via dowel 24 through a very small angle in a counter-clockwise direction. The light emitted from light source 28 in striking the mirror 20 will be deflected through an angle twice that of the mirror 20's rotation. Preferably, lead-screw 14 and angled pin 18 cause between 1 and 3 degrees of mirror rotation.

Obviously, the mechanism 10 can be utilized in both left and right-hand versions. That is to say if mirror 20 is desired to rotate in the opposite direction, a simple mirror image of mechanism 10 needs to be built.

Figure 3:
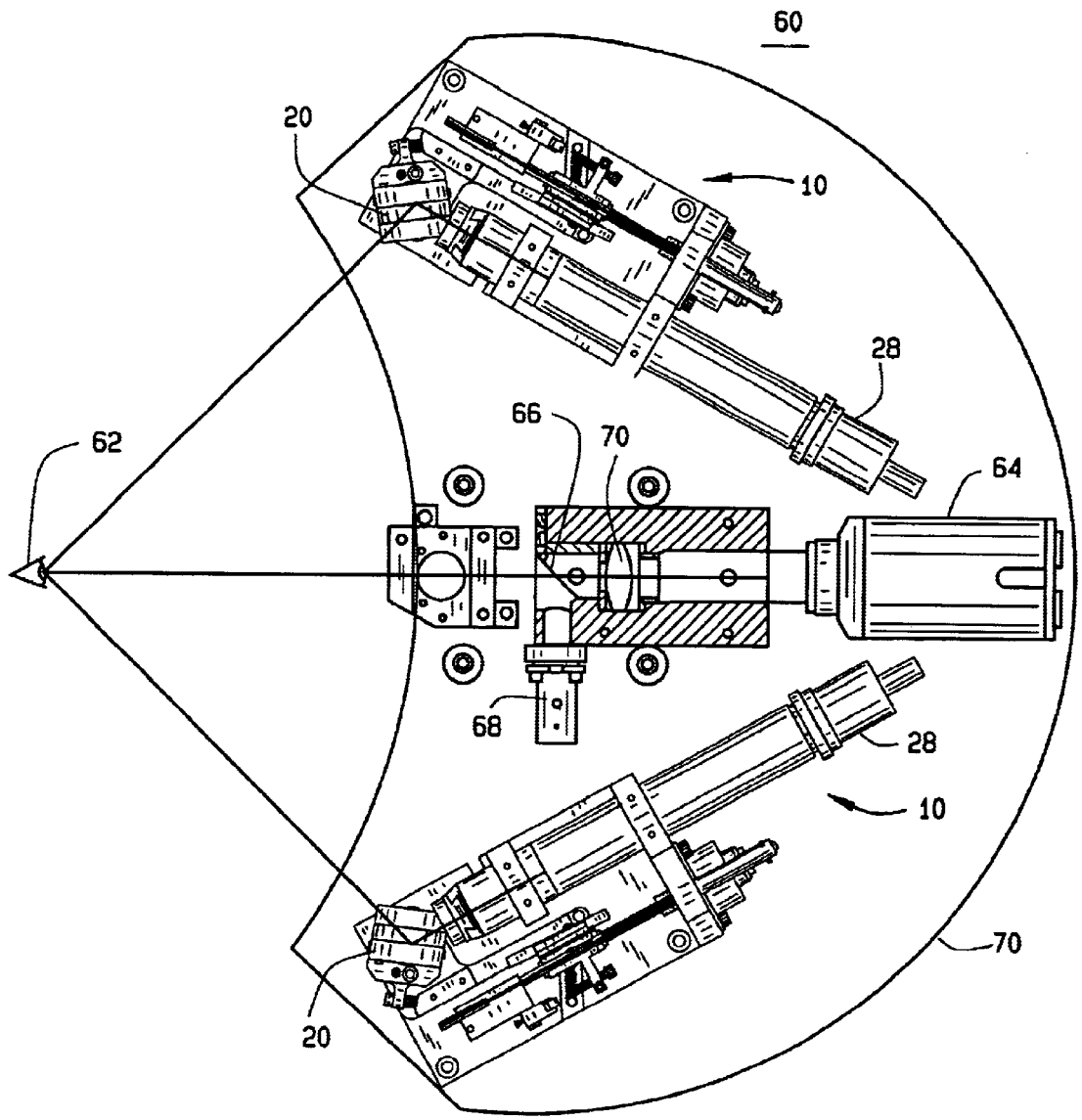
FIG. 3 is a top cut-away view of an ophthalmic system in accordance with the present invention.

FIG. 3 shows a cut away partial schematic view of an ophthalmic eye measurement system 60. Eye measurement system 60 includes two (2) mechanisms 10 as described above, including light sources 28. The light sources 28 via the mirrors 20 preferably cause a light slit to be scanned across a patient's eye 62. Images of these light slits reflected from the patient's eye are then captured by an image capture device 64, such as a video camera or other image capture means. In this way, a series of images of light reflected from the light source 28 off a patient's eye may be captured. Other parts of eye measurement 60 are common and well known in the prior art, such as beam splitter 66 and fixation source 68 as well as lens 70. Preferably the eye measurement system 60 described above is contained within housing 70 as shown.

I claim:

1. An apparatus for rotationally moving a mirror comprising:

a mirror mount including a mirror;

a pivot lever connected to the mirror mount;

a motor having a lead-screw for moving the lead-screw in a linear manner along an axis; and an elongated angled member connected to the lead-screw and abutting the pivot lever, wherein the elongated angled member is set to a non-parallel angle with respect to the lead-screw such that as the lead-screw is moved along its axis the elongated angled member causes the pivot lever to pivot and in turn, causes the mirror to rotate.

2. The invention of claim 1 further including a light source associated with the mirror mount such that upon rotation the mirror reflects the light source over a known angular range.

3. The invention of claim 2, wherein the light source is a slit light.

4. The invention of claim 1, wherein the motor is a stepper-motor for being able to rotate the mirror in discreet increments.

5. The invention of claim 1, wherein the elongated angled member is a steel pin for reducing friction between the pin and pivot lever.

6. The invention of claim 1 further includes an anti-backlash mechanism to prevent backlash from the lead-screw during movement.

7. An ophthalmic eye measurement system comprising:
   an apparatus for rotationally moving a mirror including:
      a mirror mount including a mirror;
      a pivot lever connected to the mirror mount;
      a motor having a lead-screw for moving the lead-screw in a linear manner along an axis; and
      an elongated angled member connected to the lead-screw and abutting the pivot lever, wherein the elongated angled member is set to a non-parallel angle with respect to the lead-screw such that as the lead-screw is moved along its axis the elongated angled member causes the pivot lever to pivot and in turn, causes the mirror to rotate;
   a light source associated with the mirror mount such that upon rotation the mirror reflects the light source over a known angular range; and
   an image capture device for capturing a series of images of light reflected by the light source off of a patient's eye.

8. The invention of claim 7 further including a light source associated with the mirror mount such that upon rotation the mirror reflects the light source over a known angular range.

9. The invention of claim 8, wherein the light source is a slit light.

10. The invention of claim 7, wherein the motor is a stepper-motor for being able to rotate the mirror in discreet increments.

11. The invention of claim 7, wherein the elongated angled member is a steel pin for reducing friction between the pin and pivot lever.

12. The invention of claim 7, further includes an anti-backlash mechanism to prevent backlash from the lead-screw during movement.

* * * * *